United States Patent
Locke et al.

(10) Patent No.: US 9,744,278 B2
(45) Date of Patent: Aug. 29, 2017

(54) WOUND CONNECTION PAD WITH PNEUMATIC CONNECTION CONFIRMATION ABILITY

(71) Applicant: KCI Licensing, Inc., San Antonio, TX (US)

(72) Inventors: Christopher Brian Locke, Bournemouth (GB); Benjamin A. Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 898 days.

(21) Appl. No.: 14/050,906

(22) Filed: Oct. 10, 2013

(65) Prior Publication Data
US 2014/0121615 A1   May 1, 2014

Related U.S. Application Data

(60) Provisional application No. 61/718,551, filed on Oct. 25, 2012.

(51) Int. Cl.
*A61M 1/00* (2006.01)
*A61M 13/00* (2006.01)
(Continued)

(52) U.S. Cl.
CPC ......... *A61M 1/0088* (2013.01); *A61M 1/0031* (2013.01); *A61M 2205/3344* (2013.01)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS 1,355,846 A   10/1920   Rannells
2,547,758 A   4/1951   Keeling
(Continued)

FOREIGN PATENT DOCUMENTS

AU   550575 A1   3/1986
AU   745271      4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
(Continued)

*Primary Examiner* — Tatyana Zalukaeva
*Assistant Examiner* — Ilya Treyger

(57) ABSTRACT

A system, apparatus, and method for treating a tissue site with reduced pressure includes a connector having a connector body. The connector body includes a cavity and a cavity aperture. The connector also includes a conduit port fluidly coupling a conduit to the cavity. The connector further includes a base adjacent the cavity aperture that is configured to be positioned adjacent a drape. The cavity is configured to be fluidly coupled to a manifold through an aperture of the drape. The connector also includes a sensing probe having a proximal end configured to be fluidly coupled to the conduit and a distal end extending to the cavity aperture. The distal end is configured to be positioned adjacent to and in fluid communication with a manifold.

15 Claims, 7 Drawing Sheets

(51) Int. Cl.
   A61M 27/00          (2006.01)
   A61F 13/00          (2006.01)
   A61B 17/50          (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2011/0178481 A1 | 7/2011 | Locke et al. |
| 2012/0016324 A1 | 1/2012 | Long et al. |
| 2012/0123358 A1 | 5/2012 | Hall et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009016605 A2 | 2/2009 |
| WO | 2012057881 A1 | 5/2012 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), Vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding PCT/US2013/064354 mailed Feb. 19, 2014.

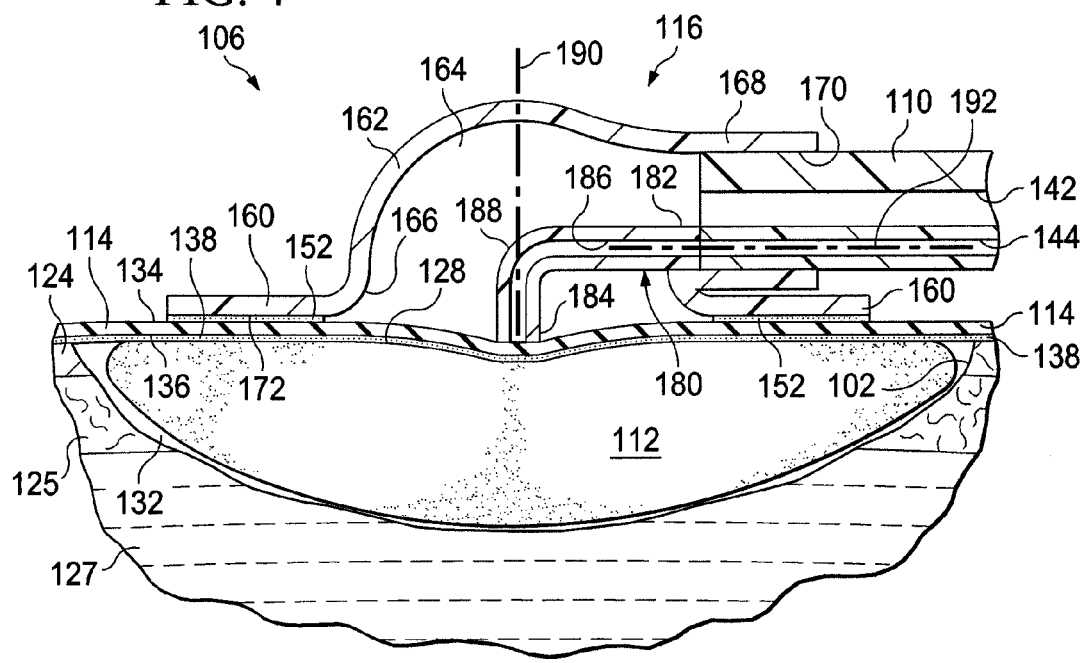
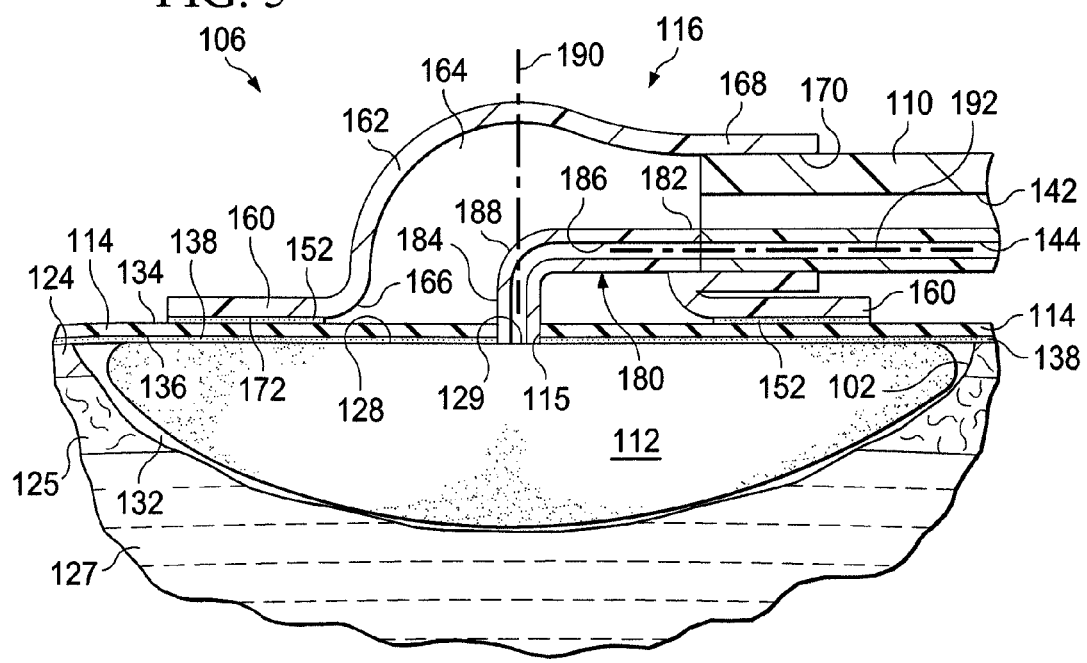

WOUND CONNECTION PAD WITH PNEUMATIC CONNECTION CONFIRMATION ABILITY

Under 35 U.S.C. §119(e), this application claims priority to and the benefit of U.S. Provisional Patent Application No. 61/718,551 filed Oct. 25, 2012, entitled "WOUND CONNECTION PAD WITH PNEUMATIC CONNECTION CONFIRMATION ABILITY," the disclosure of which is hereby incorporated by reference in its entirety.

BACKGROUND

Field of the Embodiments

The present disclosure relates generally to medical treatment systems and, more particularly, but not by way of limitation, to an apparatus, system, and method for treating a tissue site with reduced pressure involving a reduced-pressure interface.

Brief Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to the tissue site through a dressing that may include a manifold device such as a porous pad covered by a drape to maintain the reduced pressure within the wound. The porous pad contains cells or pores and distributes reduced pressure to the tissue site and channels fluids that are drawn from the tissue site. In order for the patient to receive the benefits of the reduced pressure therapy, the reduced pressure must be correctly supplied to the manifold device. During some treatments, a caregiver preparing the reduced pressure treatment may improperly apply the dressings over the wound so that the reduced pressure is not properly applied to the manifold device. Therefore, there is a need for a system, method, and apparatus that provides notification to the caregiver of improper administration of reduced pressure.

SUMMARY

These and other problems are generally solved or circumvented, and technical advantages are generally achieved, by embodiments that provide a wound connection pad with pneumatic connection confirmation ability.

In accordance with an embodiment, a system for treating a tissue site with reduced pressure is described. The system may include a manifold configured to be placed proximate to the tissue site and a drape configured to cover the manifold. The system may further include a conduit having a primary lumen and a secondary lumen and a connector. The connector may include a connector body having a cavity. The cavity may be configured to be coupled to the manifold through an aperture in the drape. The connector may also include a conduit port that is configured to receive the conduit and to couple the primary lumen to the cavity. The connector may also include a sensing probe coupled to the conduit port. The sensing probe may be configured to couple the secondary lumen to the manifold through the cavity and the aperture in the drape.

In accordance with another embodiment, a system for treating a tissue site with reduced a pressure is described. The system may include a manifold configured to be placed proximate to the tissue site and a drape configured to cover the manifold. The drape may be configured to have an aperture formed therein. The system may also include a reduced-pressure source and a conduit. The conduit may include a primary lumen having a first end configured to receive reduced pressure from the reduced-pressure source and a second end. The conduit may also have at least one secondary lumen having a first end configured to be fluidly coupled to a pressure sensor and a second end. The system may further include a connector configured to provide reduced pressure through the drape to the manifold. The connector may include a connector body having a cavity. The cavity may have a cavity aperture at a first end of the connector body. The connector may also include a conduit port extending from a second end of the connector body. The conduit port may be configured to fluidly couple the second end of the primary lumen and the second end of the at least one secondary lumen to the connector body. The connector may also have a base extending from a peripheral portion of the connector body adjacent to the cavity aperture. The base may be configured to be positioned adjacent to the drape. The cavity may be configured to be fluidly coupled to the manifold through the aperture of the drape. The connector may further include a sensing probe having a proximal end configured to be fluidly coupled to the at least one secondary lumen. The sensing probe may also have a distal end extending to the cavity aperture. The distal end may be configured to be positioned adjacent to and in fluid communication with the manifold.

In yet another embodiment, a connector for fluidly coupling a conduit and a manifold of a reduced-pressure treatment system is described. The connector may include a connector body having a cavity including a cavity aperture at a first end of the connector body. The connector may also include a conduit port extending from a second end of the connector body. The conduit port may be configured to fluidly couple an end of a primary lumen of the conduit to the cavity. The conduit port may also be configured to fluidly couple an end of at least one secondary lumen to the connector body. The connector may also include a base extending from a peripheral portion of the connector body adjacent to the cavity aperture. The base may be configured to be positioned adjacent to a drape covering the manifold. The cavity may be configured to be fluidly coupled to the manifold through an aperture formed in the drape. The connector may further include a sensing probe having a proximal end configured to be fluidly coupled to the at least one secondary lumen. The sensing probe may also include a distal end extending to the cavity aperture. The distal end may be configured to be positioned adjacent to and in fluid communication with the manifold.

In still another embodiment, a connector for fluidly coupling a conduit and a manifold of a reduced-pressure treatment system is described. The connector may include a connector body having a cavity. The cavity may be configured to be fluidly coupled to the manifold through an aperture in a drape. The connector may also include a conduit port coupled to the connector body. The conduit port may be configured to receive the conduit and to fluidly couple a primary lumen to the cavity. The connector may further include a sensing probe pneumatically coupled to the conduit port. The sensing probe may be configured to pneumatically couple a secondary lumen to the manifold through the cavity and the aperture in the drape.

In another embodiment, a connector for fluidly coupling a manifold to a reduced-pressure source is described. The connector may include a base having an aperture and a conduit port configured to receive a primary lumen and a secondary lumen. The connector may also include a connector body having a cavity fluidly coupling the aperture to the conduit port. The connector may further include a sensing probe disposed in the cavity. The sensing probe may be pneumatically coupled to the aperture and to the conduit port.

In yet another embodiment, a method for applying reduced pressure to a tissue site with a reduced-pressure system is described. The method may prepare a tissue site with a dressing having an aperture to expose a portion of a manifold of the dressing. The method may couple a connector proximate to a first side of the dressing. The connector may include a sensing probe having a distal end proximate to a medial portion of the connector. The method may position the distal end of the sensing probe proximate to the aperture of the dressing so that the distal end is positioned adjacent to and in fluid communication with the manifold. The method may supply reduced pressure to the connector with a reduced-pressure source and determine if the sensing probe and the supply of reduced pressure are pneumatically coupled. If the sensing probe and the supply of reduced pressure are pneumatically coupled, the method may continue to supply reduced pressure. If the sensing probe and the supply of reduced pressure are not pneumatically coupled, the method may indicate improper application of reduced pressure.

In still another embodiment, a method for coupling a manifold to a reduced-pressure source is described. The method may dispose the manifold proximate to a tissue site and may cover the manifold with a sealing member. The method may position a cavity and a sensor probe of a reduced-pressure interface over an opening in the sealing member. The method may couple the reduced-pressure interface to the sealing member so that the cavity is coupled to the manifold through the opening in the sealing member and the sensor probe is coupled to the manifold through the opening in the sealing member. The method may couple the reduced-pressure source to the cavity. The method may couple the sensor probe to a pressure sensor.

BRIEF DESCRIPTION OF THE DRAWINGS

Illustrative embodiments are described in more detail below with reference to the attached figures, which are incorporated by reference herein and wherein:

FIG. 4 is a cross-sectional view of the reduced-pressure interface of FIG. 2A in a second failure mode in accordance with an embodiment;

FIG. 5 is a cross-sectional view of the reduced-pressure interface of FIG. 2A in a third failure mode in accordance with an embodiment;

DETAILED DESCRIPTION OF ILLUSTRATIVE EMBODIMENTS

New and useful systems, methods, and apparatuses associated with reduced pressure interfaces used for regulating pressure are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Unless otherwise indicated, values of pressure stated herein are gauge pressures. References to increases in reduced pressure typically refer to a decrease in absolute pressure, and decreases in reduced pressure typically refer to an increase in absolute pressure.

Figure 1:
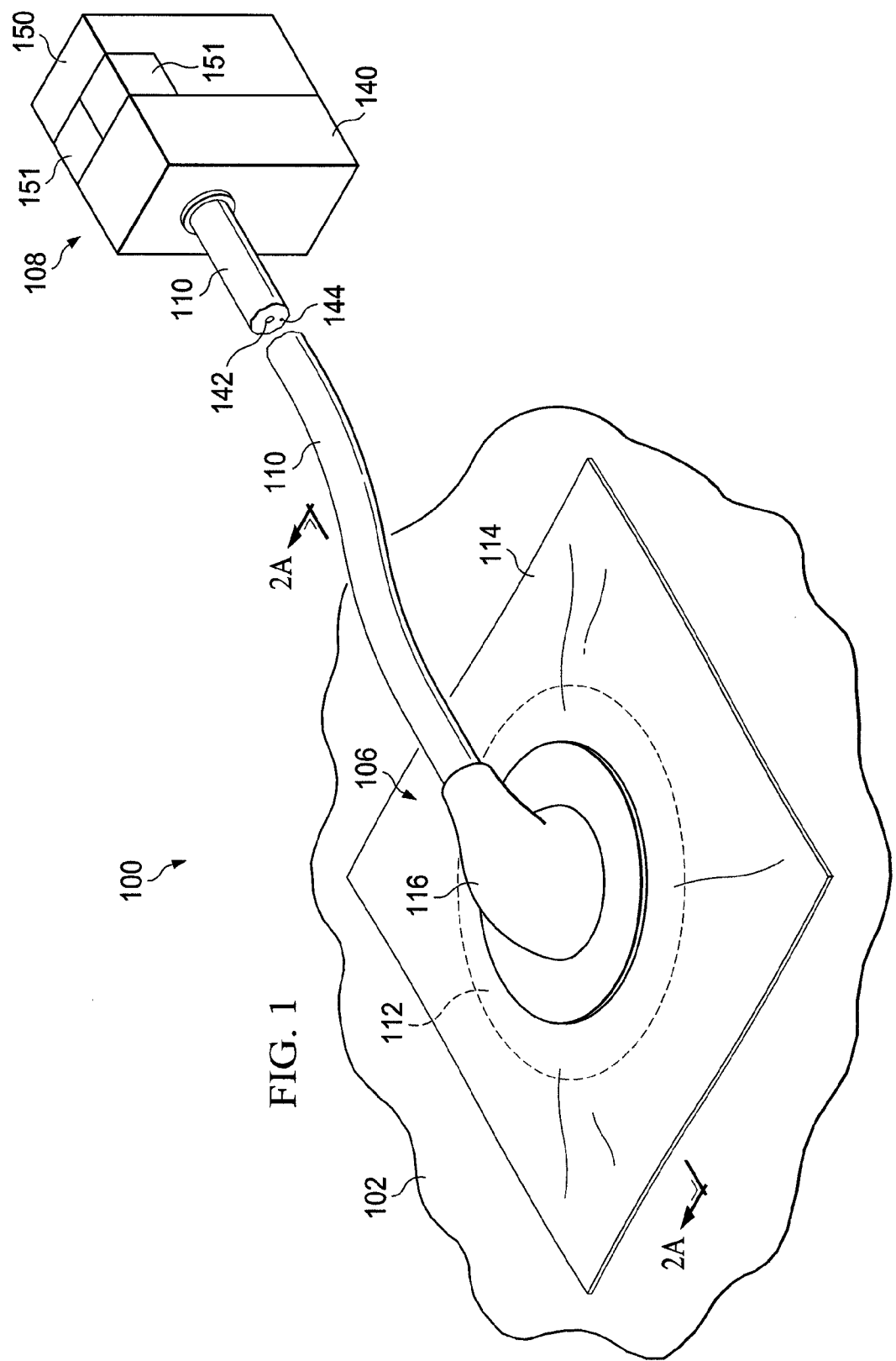
FIG. 1 is a perspective view of a system for treating a tissue site on a patient with reduced pressure in accordance with an embodiment.

FIG. 1 is a perspective view illustrating a system 100 for treating a tissue site 102 on a patient with reduced pressure. The system 100 may include a dressing 106 for supplying reduced pressure to the tissue site 102. The dressing 106 may be disposed proximate to the tissue site 102. The system 100 also includes a treatment unit 108 and a conduit 110 fluidly connected between the dressing 106 and the treatment unit 108. The treatment unit 108 may supply reduced pressure through the conduit 110 to the dressing 106 at the tissue site 102. In an illustrative embodiment, the dressing 106 may further include a reduced-pressure interface, such as a connector. 116, and a manifold 112 (see also FIGS. 2A, 2B, and 2C) wherein the connector 116 fluidly couples the conduit 110 to the manifold 112 for distributing reduced pressure at the tissue site 102. The dressing 106 may also include a drape 114 for covering the tissue site 102 and providing a seal between the connector 116 and the manifold 112.

The treatment unit 108 may include a liquid-collection chamber, or a collection canister, a reduced-pressure source 140, and an instrumentation unit 150. The reduced-pressure source 140 may be housed within or used in conjunction with the treatment unit 108. In an illustrative embodiment, the reduced-pressure source 140 may be an electrically-driven vacuum pump. In another illustrative embodiment, the reduced-pressure source 140 may be a manually-actuated or manually-charged pump that does not require electrical power. The reduced-pressure source 140 may be other types of reduced pressure pumps, or may be a wall suction port such as those available in hospitals and other medical facilities.

The instrumentation unit 150 may be in fluid communication with the reduced-pressure source 140. The instrumentation unit 150 may include a microprocessor adapted to process pressure signals received by the conduit 110, monitor the pressure signals, and issue alerts according to a pre-determined pressure therapy for a patient. The pre-determined pressure therapy may include a pressure profile of desired target pressures to be provided to a patient over a time period. The pressure profile may include a set-up profile applying target pressures at the commencement of therapy treatments and a maintenance profile for applying target pressure during therapy. The instrumentation unit 150 may include sensors, processing units, alarm indicators, memory, databases, software, display units, and user interfaces that further facilitate the application of reduced pressure treatment to the tissue site 102.

In one illustrative embodiment, pressure sensors 151 located in the instrumentation unit 150 may be disposed at or near the reduced-pressure source 140. In another illustrative embodiment, the pressure sensors 151 may be one or more transducers located in the connector 116. The pressure sensors 151 include an electrical interface (not shown) that provides the pressure signal measured at or near the reduced-pressure source 140. The pressure signal provides an indication of the pressure between the connector 116 and the manifold 112 as described in more detail below. The pressure sensors 151 may communicate with a processing unit, such as the instrumentation unit 150, that monitors and controls the reduced pressure that may be delivered by the reduced-pressure source 140. In an illustrative embodiment, the pressure sensors 151 communicate with the instrumentation unit 150 to monitor whether the pressure signal may be following a pressure set-up profile. The pressure set-up profile may include an expected increase in the reduced pressure detected at the tissue site 102 following initial application of reduced pressure. In the event the pressure signal does not follow the pressure set-up profile within a predetermined time period, the instrumentation unit 150 provides an indication that the pressure signal did not follow the pressure set-up profile within the predetermined time period. In an illustrative example, the indication may be in the form of a visual or audible alert or alarm. In the event the pressure signal is following the pressure set-up profile, the instrumentation unit 150 may provide an indication that the pressure signal followed the pressure set-up profile. The indication that the pressure set-up profile has been followed may be different than the indication that the pressure set-up profile has not been followed.

Figure 2A:
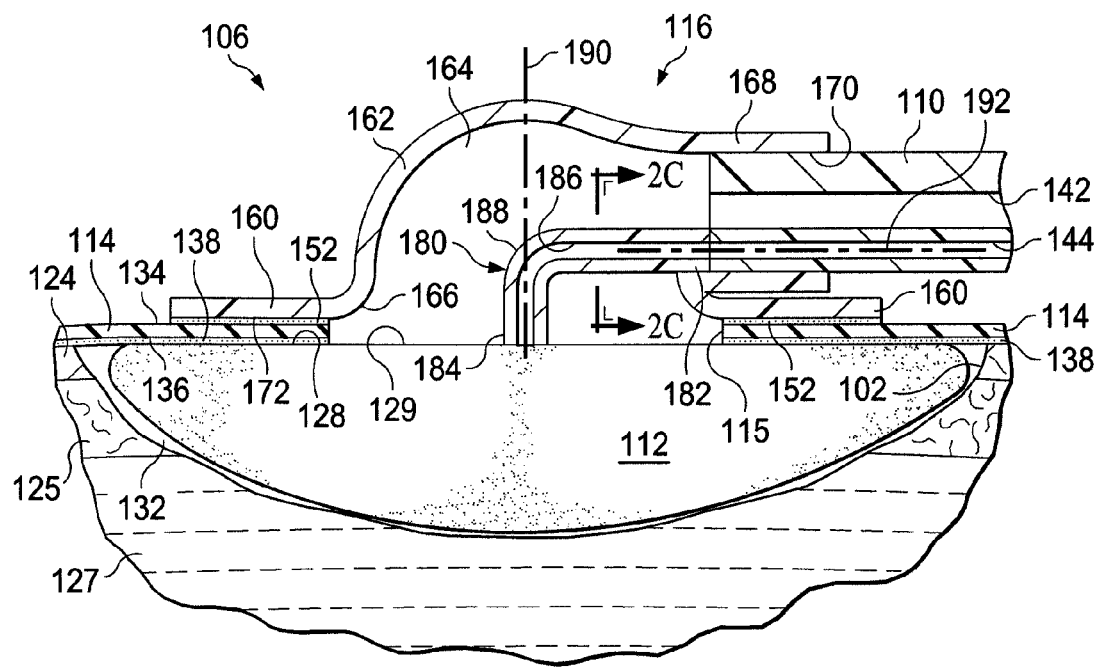
FIG. 2A is a cross-sectional view of a reduced-pressure interface of the system of FIG. 1, taken along line 2A-2A in accordance with an embodiment.

FIG. 2A is a sectional view of a portion of the system 100 disposed at the tissue site 102 and illustrating additional details of the connector 116. The system 100 may be used for various different types of tissue sites 102. The term "tissue site" in this context broadly refers to a wound or defect located on or within tissue of a human, animal, or other organism, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, grafts, and fistulas, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location. The term "tissue site" may also include incisions, such as a surgical incision. The tissue site 102, may include an epidermis 124, subcutaneous tissue 125, or other muscle tissue 127. The tissue site 102 may be surrounded by healthy or undamaged tissue, for example a portion of the epidermis 124 that may be undamaged. Treatment of the tissue site 102 may include removal of fluids, for example, exudates or ascites.

In the illustrated embodiment, the manifold 112 may be positioned proximate to the tissue site 102 such that the manifold 112 has a first surface that faces the tissue site 102 and a second surface that may be opposite the first surface. As described in more detail below, the second surface may have a first portion, such as covered portion 128, and a second portion, such as exposed portion 129. The term "manifold" as used herein generally refers to a substance or structure that may be provided to assist in applying reduced pressure to, delivering fluids to, or removing fluids from the tissue site 102. The manifold 112 may include a plurality of flow channels or pathways that distribute fluids provided to and removed from the tissue site 102. In one illustrative embodiment, the flow channels or pathways may be interconnected to improve distribution of fluids provided to or removed from the tissue site 102. The manifold 112 may be a biocompatible material that may be capable of being placed in contact with the tissue site 102 and distributing reduced pressure to the tissue site 102. Examples of the manifold 112 may include, without limitation, devices that have structural elements arranged to form flow channels, such as, for example, cellular foam, open-cell foam, porous tissue collections, liquids, gels, and foams that include, or cure to include, flow channels. The manifold 112 may be porous and may be made from foam, gauze, felted mat, or other material suited to a particular biological application. In one embodiment, the manifold 112 may be a porous foam and may include a plurality of interconnected cells or pores that act as flow channels. The porous foam may be a polyurethane, open-cell, reticulated foam such as Granu-Foam® material manufactured by Kinetic Concepts, Incorporated of San Antonio, Tex. In some embodiments, the manifold 112 may also be used to distribute fluids such as medications, antibacterials, growth factors, and other solutions to the tissue site 102. Other layers may be included in or on the manifold 112, such as absorptive materials, wicking materials, hydrophobic materials, and hydrophilic materials.

In one illustrative embodiment, the manifold 112 may be constructed from bioresorbable materials that do not have to be removed from the tissue site 102 following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 112 may further serve as a scaffold for new cell-growth, or a scaffold material may be used in conjunction with the manifold 112 to promote cell-growth. A scaffold may be a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 114 has a first side 134 and a second side 136 partially covering the surface portion 128 of the manifold 112 when positioned over the tissue site 102, and a drape aperture 115 extending through the drape 114, creating the exposed portion 129 and the covered portion 128 of the second surface of the manifold 112. The drape 114 may be a material that provides a fluid seal. "Fluid seal," or "seal," means a seal adequate to maintain reduced pressure at a desired site given the particular reduced-pressure source or subsystem involved. The drape 114 may be, for example, an impermeable or semi-permeable, elastomeric material. "Elastomeric" means having the properties of an elastomer. Elastomer generally refers to a polymeric material that may have rubber-like properties. More specifically, most elastomers may have ultimate elongations greater than 100% and a significant amount of resilience. The resilience of a material refers to the material's ability to recover from an elastic deformation. Elastomers that are relatively less resilient may also be used as these elastomers may be more likely to tear when faced with a cutting element. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of materials of the drape 114 may include a silicone drape, 3M Tegaderm® drape, and a polyurethane (PU) drape such as one available from Avery Dennison Corporation of Pasadena, Calif. An additional, specific non-limiting example of a material of the drape 114 may include a 30 μm matt polyurethane film such as the Inspire™ 2317 manufactured by Exopack™ Advanced Coatings of Matthews, N.C.

A drape adhesive 138 may be positioned between the second side 136 of the drape 114 and a portion of the epidermis 124 surrounding the tissue site 102 that may be intact. The drape adhesive 138 may hold the drape 114 in place and may aid the drape 114 to maintain reduced pressure in a sealed space 132 by fluidly sealing the drape 114 to the epidermis 124 surrounding the tissue site 102. Fluidly sealing the drape 114 to the epidermis 124 may refer to sealing of the drape 114 to the epidermis 124 so that fluid may be inhibited from passing between the drape 114 and the epidermis 124. The drape adhesive 138 may include another layer such as, for example, a gasket or additional sealing member. The drape adhesive 138 may take numerous forms. For example, the drape adhesive 138 may be a medically acceptable adhesive, such as a pressure-sensitive adhesive, that extends about a portion of, a periphery of, or about all of the drape 114; a double-sided drape tape; a paste; a hydrocolloid; a hydro-gel; a silicone gel; an organogel; or other sealing devices or elements. The drape adhesive 138 may also be a sealing ring or other device. In still another example, the drape adhesive 138 may be a releasable adhesive material capable of being removed from the tissue site 102 and reapplied to the tissue site 102. The drape adhesive 138 may be disposed on the second side 136 of the drape 114. Before use, the drape adhesive 138 may be covered by a release liner (not shown) to protect the attachment material 138 before being applied to the tissue site 102.

The connector 116 may include a base 160 and a connector body 162 having a cavity 164. In some embodiments, the base 160 may be coupled to one end of the connector body 162, extending from a peripheral portion of the connector body 162. The base 160 may be adjacent a portion of the cavity 164. The connector 116 may further include a cavity aperture 166 at one end of the connector body 162. For example, the cavity aperture 166 may be formed through or part of the base 160. A conduit port 168 may be coupled to the other end of the connector body 162. In some embodiments, for example, the conduit port 168 may extend from the connector body 162 as shown in FIG. 2A. The conduit port 168 may be fluidly coupled to the cavity 164. The conduit port 168 may include an aperture 170 for receiving a conduit, such as the conduit 110. When the connector 116 is positioned at the tissue site 102, the base 160 may be positioned adjacent the first side 134 of the drape 114 over the manifold 112 so that the cavity 164 is fluidly coupled to the exposed portion 129 of the manifold 112 through the drape aperture 115 of the drape 114. The base 160 may be coupled to the first side 134 of the drape 114 by a base adhesive 152 that holds the connector 116 in place on the drape 114. The base adhesive 152 may be similar to the drape adhesive 138. In some embodiments, the base adhesive 152 may have releasable characteristics allowing for the connector 116 to be removed from and reapplied to the drape 114.

As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling may mean that fluid may be in communication between the designated parts or locations. Pneumatic coupling may mean, in part, that gas or gas pressure may be in communication between the designated parts or locations.

The conduit 110 may be a multi-lumen conduit having a primary lumen 142 and a secondary lumen 144. The conduit 110 may have different shapes and include more or fewer primary lumens 142 and secondary lumens 144. The primary lumen 142 may deliver reduced pressure, and the secondary lumen 144 may function as a sensing lumen. When the conduit 110 is disposed within the aperture 170, the primary lumen 142 and the secondary lumen 144 may be in fluid communication with the cavity 164. As the primary lumen 142 provides reduced pressure to the tissue site 102, exudates and other fluids may be drawn through the primary lumen 142. The secondary lumen 144 may be configured to be fluidly isolated from the primary lumen 142 so as not to interfere with the process of sensing the pressure. Liquids or exudates communicated through the primary lumen 142 may be removed from the conduit 110 and may be retained within a liquid-collection chamber (not shown) fluidly coupled to the conduit 110. In some embodiments, the secondary lumen 144 may fluidly communicate pressure at a terminal end of the conduit 110 within the connector 116 to the pressure sensors 151. The pressure communicated by the secondary lumen 144 may be representative of the pressure at the tissue site 102.

In one illustrative embodiment, the connector 116 may be a T.R.A.C.® Pad or Sensa T.R.A.C.® Pad available from KCI of San Antonio, Tex., modified as described in more detail below. The connector 116 may fluidly couple the reduced pressure provided by the primary lumen 142 to the manifold 112 through the drape aperture 115 of the drape 114. The manifold 112 may distribute the reduced pressure to the sealed space 132 formed by the drape 114 and the tissue site 102. Thus, the connector 116 allows reduced pressure to be delivered to the tissue site 102. In an illustrative example, the reduced pressure may be between −5 mm Hg (−667 Pa) and −500 mm Hg (−66.7 kPa) and between −75 mm Hg (−9.9 kPa) and −300 mm Hg (−39.9 kPa).

The reduced pressure connector 116 may be made of a semi-rigid material that may be capable of collapsing under a force. In a non-limiting example, the connector 116 may be made from a plasticized polyvinyl chloride (PVC), polyurethane, cyclic olefin copolymer elastomer, thermoplastic elastomer, poly acrylic, silicone polymer, or polyether block amide copolymer. The reduced pressure connector 116 may be formed of a semi-rigid material that collapses when under reduced pressure less than a threshold pressure.

Figure 2B:
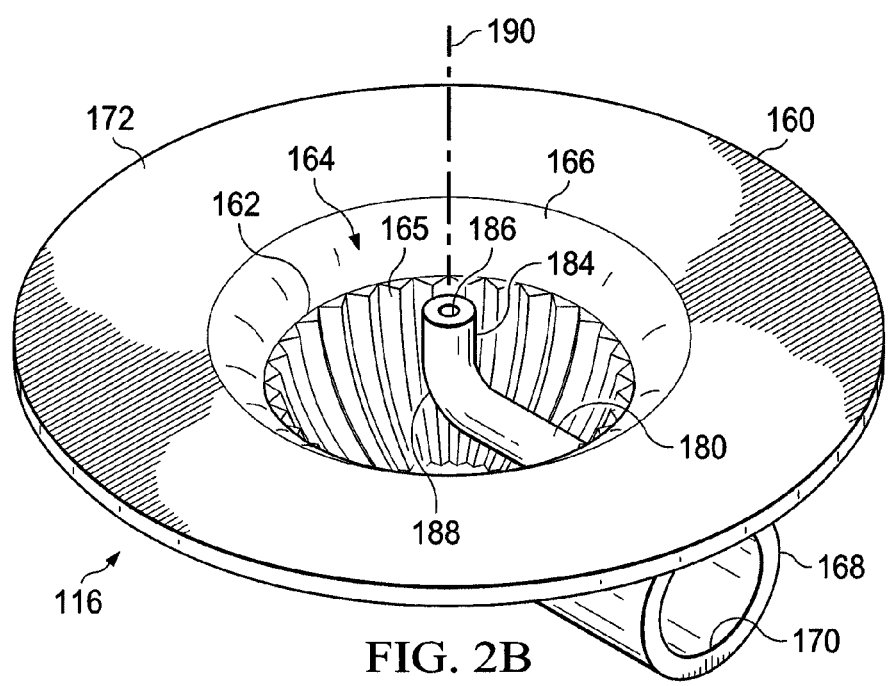
FIG. 2B is a perspective bottom view of the reduced-pressure interface of FIG. 2A illustrating additional details of the reduced-pressure interface in accordance with an embodiment.

FIG. 2B is a bottom perspective view of the connector 116 illustrating additional details that may be associated with some embodiments. In some embodiments, the connector 116 may include one or more channels 165 formed on portions of the inside surfaces of the connector body 162 within the cavity 164. The channels 165 may extend between the base 160 and the conduit port 168. The channels 165 may direct the flow of fluids and exudates from the tissue site 102 and the manifold 112 to the conduit port 168 and into the primary lumen 142, which returns the fluids to the treatment unit 108 for storage or disposal.

Referring to FIG. 2A and as indicated above, the primary lumen 142 may be fluidly coupled to the manifold 112 by the cavity 164 of the connector 116 through the drape aperture 115 of the drape 114. In some embodiments, the drape aperture 115 may be approximately the same size as the cavity aperture 166 of the cavity 164 to facilitate fluid communication between the primary lumen 142 and the manifold 112. In some embodiments, the drape 114 may come with the drape aperture 115 preformed. In some embodiments, the drape aperture 115 is formed prior to the drape 114 being applied to the tissue site 102. If the drape aperture 115 of the drape 114 may be too small, fluid flow between the manifold 112 and the connector 116 may be partially or fully blocked. If fluid flow is partially or fully blocked, the reduced pressure provided by the primary lumen 142 may not be pneumatically coupled to the tissue site 102. Additionally, if the drape aperture 115 of the drape 114 is properly sized, the cavity aperture 166 should be concentrically aligned with the drape aperture 115 when the base 160 is coupled to the drape 114. If the cavity aperture 166 is misaligned with the drape aperture 115, fluid flow between the manifold 112 and the connector 116 may be partially or fully blocked. If fluid flow is partially or fully blocked, the reduced pressure provided by the primary lumen 142 may not pneumatically coupled to the tissue site 102. If the primary lumen 142 is not pneumatically coupled to the tissue site 102, the system 100 may provide no reduced-pressure therapy or inadequate reduced-pressure therapy.

As indicated above, the secondary lumen 144 may be fluidly coupled to the cavity 164 of the connector 116. If the "blockage conditions" previously described occur, the primary lumen 142 may become pneumatically coupled to the secondary lumen 144 rather than to the manifold 112 and the tissue site 102. If the primary lumen 142 and the secondary lumen 144 are pneumatically coupled, the secondary lumen 144 may provide the pressure sensors 151 with a pressure indicating that the tissue site 102 has reached the desired target pressure. Even though the reduced pressure is not being supplied to the tissue site 102, the reduced pressure may be supplied to the cavity 164, and the pressure sensors 151 may be measuring the pressure in the cavity 164 via the secondary lumen 144. To correct the blockage condition, the drape 114 may be removed, and the drape aperture 115 may be resized or the connector 116 may be repositioned to allow fluid flow between the cavity 164 and the sealed space 132. It may be desirable to correct these blockage conditions during the setup procedures before commencing therapeutic treatments. Thus, it may be desirable that the drape adhesive 138 and the base adhesive 152 be releasable so that both the drape 114 and the connector 116 can be reapplied after the blockage condition is corrected.

In one embodiment for detecting such blockage conditions, the connector 116 may also include a sensing probe 180. The sensing probe 180 may be fluidly coupled between the secondary lumen 144 and the exposed surface 129 of the manifold 112. In some embodiments, the sensing probe 180 may have a probe lumen 186. The probe lumen 186 may have an aperture at each end of the sensing probe 180. The sensing probe 180 may have a proximal end 182 configured to be positioned adjacent to the secondary lumen 144 of the conduit 110. The sensing probe 180 may also have a distal end 184 extending into the cavity 164 of the connector body 162. The distal end 184 may be configured to be positioned adjacent the exposed surface 129 of the manifold 112.

Figure 2C:
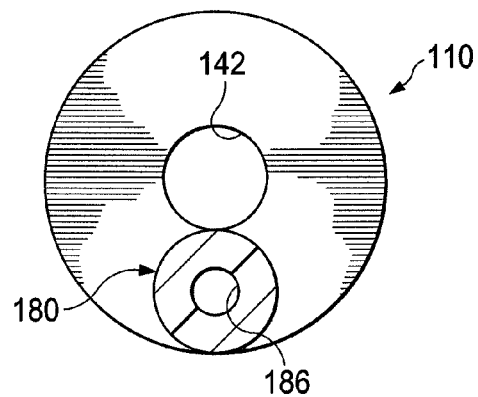
FIG. 2C is a cross-sectional view of a portion of the reduced-pressure interface of FIG. 2A taken along line 2C-2C in accordance with an embodiment.

FIG. 2C is a sectional view of a portion of the connector 116 taken along line 2C-2C of FIG. 2A, illustrating additional details that may be associated with some embodiments. The secondary lumen 144 may fluidly couple to the probe lumen 186 so that a fluid path provided by the secondary lumen 144 may extend past a terminus of the primary lumen 142 through the probe lumen 186. Referring to FIGS. 2A and 2C, the aperture of the probe lumen 186 of the distal end 184 of the sensing probe 180 may extend from the cavity 164 to a plane occupied by the base 160. In some embodiments, the aperture of the probe lumen 186 of the distal end 184 of the sensing probe 180 may extend from the cavity 164 past the plane occupied by the base 160. When the connector 116 is positioned at the tissue site 102, the aperture of the probe lumen 186 of the distal end 184 of the sensing probe 180 may be proximate to or in contact with the manifold 112. Thus, the probe lumen 186 may fluidly couple the secondary lumen 144 to the manifold 112 rather than to the cavity 164 of the connector body 162. The probe lumen 186 pneumatically separates the primary lumen 142 and the secondary lumen 144 to minimize the risk of pressure readings that may not be not representative of pressure in the sealed space 132. The secondary lumen 144 and the primary lumen 142 may be pneumatically coupled when the sealed space 132 is open to allow fluid communication between the primary lumen 142, the sealed space 132 occupied by the manifold 112, and the secondary lumen 144. In some embodiments, the connector 116 may be coupled to the drape 114 so that the distal end 184 of the sensing probe 180 is aligned with a medial portion of the drape aperture 115 of the drape 114. In addition, the distal end 184 of the sensing probe 180 may contact the exposed portion 129 of the manifold 112. In some embodiments, the sensing probe 180 includes an elbow 188 that may be configured to position the distal end 184 of the sensing probe 180 proximate to the plane occupied by the base 160. The elbow 188 may turn the sensing probe 180 so that the distal end 184 is located in a plane that forms an angle with a plane occupied by the proximal end 182. In some embodiments, the elbow 188 may be a 90° elbow. In some embodiments, the elbow 188 may have a radius of curvature between about 30° and about 120°.

During operation, if reduced pressure is supplied to the primary lumen 142, the primary lumen 142 may supply the reduced pressure to the cavity 164 and to the manifold 112 through the drape aperture 115 of the drape 114. The reduced pressure supplied to the cavity 164 and the manifold 112 may draw fluids from the tissue site 102 through the manifold 112 and into the cavity 164 where the primary lumen 142 may conduct the fluids away from the tissue site 102 for disposal. The supply of reduced pressure to the cavity 164 may also be pneumatically coupled to the probe lumen 186 through the manifold 112. The instrumentation unit 150 may identify that the primary lumen 142 and the secondary lumen 144 are pneumatically coupled through the manifold 112 and the probe lumen 186 in response to the pressure signal from the pressure sensors 151. The pressure at exposed portion 129 of the manifold 112 may be pneumatically communicated through the probe lumen 186 and the secondary lumen 144 to the pressure sensors 151. Thus, the sensing probe 180 can aid in determining whether the system 100 may be operating properly to supply reduced pressure to the tissue site 102. In addition, the sensing probe 180 may aid in placement of the connector 116 by acting as a visual guide for alignment of the connector 116 relative to the drape aperture 115 of the drape 114. When positioning the connector 116 at the tissue site 102, the distal end 184 of the sensing probe 180 may be aligned with a medial portion of the drape aperture 115 to concentrically align the cavity aperture 166 with the drape aperture 115. In an illustrative embodiment, the manifold 112 may filter fluids away from the distal end 184 of the sensing probe 180 to prevent entry of fluid from the tissue site 102 into the probe lumen 186 and the secondary lumen 144.

Figure 3:
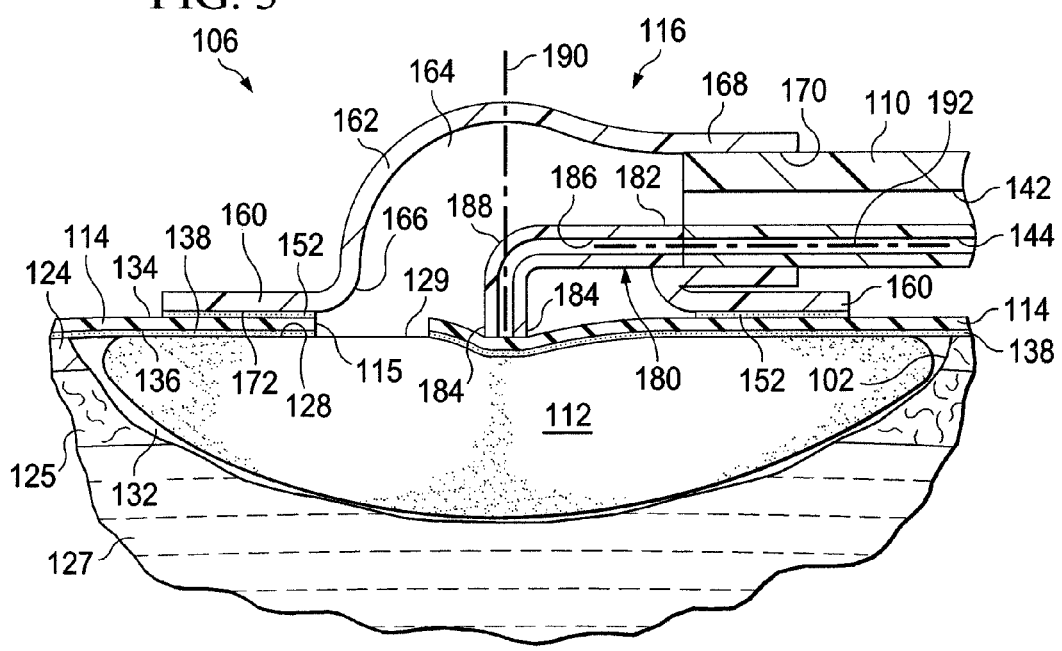
FIG. 3 is a cross-sectional view of the reduced-pressure interface of FIG. 2A in a first failure mode in accordance with an embodiment.

The sensing probe 180 may also aid in the determination of improper or failed operation of the connector 116 and the dressing 106. For example, FIG. 3 is a side sectional view of the dressing 106 disposed at the tissue site 102, illustrating additional details of the connector 116 in a first failure mode. As shown in FIG. 3, the dimensions of the drape aperture 115 may be larger than a dimension of the distal end 184 of the sensing probe 180. The dimensions of the drape aperture 115 may also be smaller than a dimension of the cavity aperture 166. For example, the drape aperture 115, the distal end 184, and the cavity aperture 166 may all be substantially circular. In the first failure mode, the drape aperture 115 may have a circumference that may be larger than a circumference of the distal end 184 but smaller than a circumference of the cavity aperture 166. In addition, the distal end 184 may not be aligned with a medial portion of the drape aperture 115. Consequently, when the connector 116 is secured to the drape 114, a portion of the drape 114 may be disposed between the distal end 184 of the sensing probe 180 and the manifold 112. The portion of the drape 114 may block or partially block the cavity aperture 166. If reduced pressure is supplied through the primary lumen 142, the portion of the drape 114 between the distal end 184 of the sensing probe 180 and the manifold 112 may block fluid communication with the probe lumen 186. As a consequence, the secondary lumen 144 may not be pneumatically coupled to the primary lumen 142 through the sensing probe 180. The instrumentation unit 150 (FIG. 1) may detect the failure of the primary lumen 142 and the secondary lumen 144 to pneumatically couple with the pressure sensors 151, and the instrumentation unit 150 may provide an indication or error message near the start of the application of reduced pressure. In addition, as the drape aperture 115 is smaller than the cavity aperture 166, the tissue site 102 may receive a reduced pressure that may be less than the desired reduced pressure for reduced-pressure therapy.

FIG. 4 is a side sectional view of a portion of the system 100 disposed at the tissue site 102, illustrating additional details of the connector 116 in a second failure mode of the system 100. As shown in FIG. 4, the drape aperture 115 was not formed in the drape 114. Consequently, when the connector 116 is secured to the drape 114, the drape 114 may block fluid communication between the cavity aperture 166 and the manifold 112. In addition, the drape 114 may block fluid communication between the probe lumen 186 and the manifold 112. If the reduced pressure is supplied through the primary lumen 142, the portion of the drape 114 between the distal end 184 of the probe lumen 186 and the manifold 112 may be drawn into contact with the distal end 184. Contact between the drape 114 and the distal end 184 may prevent pneumatic coupling of the primary lumen 142 and the secondary lumen 144 through the probe lumen 186. As a consequence, the probe lumen 186 and the secondary lumen 144 may not communicate a reduced pressure to the sensors 151. The instrumentation unit 150 may then provide an indication or error message that no pneumatic coupling has occurred. During the second failure mode of the system 100, no reduced pressure may be supplied to the tissue site 102.

FIG. 5 is a side sectional view of a portion of the system 100 disposed at the tissue site 102, illustrating additional details of the connector 116 in a third failure mode. As shown in FIG. 5, a dimension of the drape aperture 115 may be larger than a dimension of the distal end 184 of the sensing probe 180. The dimension of the drape aperture 115 may also be smaller than a dimension of the cavity aperture 166. For example, the drape aperture 115, the distal end 184, and the cavity aperture 166 may all be substantially circular. In the third failure mode, the drape aperture 115 may have a circumference that may be larger than a circumference of the distal end 184 but smaller than a circumference of the cavity aperture 166. Unlike the first failure mode of FIG. 3, in the third failure mode of FIG. 5, the distal end 184 may be aligned with a medial portion of the drape aperture 115. Consequently, when the connector 116 is secured to the drape 114, the distal end 184 of the sensing probe 180 may contact the exposed portion 129 of the manifold 112. A portion of the drape 114 may block or partially block the cavity aperture 166. If reduced pressure is supplied through the primary lumen 142, the drape 114 may prevent fluid communication of the reduced pressure to the manifold 112. The probe lumen 186, being in fluid communication with the manifold 112 through the drape aperture 115, may not be in fluid communication with the cavity 164 because the cavity aperture 166 is blocked by the portion of the drape 114. As a result, the primary lumen 142 and the secondary lumen 144 may not be pneumatically coupled by the probe lumen 186. As a consequence, the probe lumen 186 and the secondary lumen 144 may not communicate a reduced pressure to the sensors 151 that indicates that reduced-pressure is being provided to the sealed space 132. In some cases, the primary lumen 142 and the secondary lumen 144 may pneumatically couple through the sensing probe 180, but reduced pressure communicated by the probe lumen 186 and the secondary lumen 144 may not be the expected pressure for the proper application of reduced-pressure therapy. The instrumentation unit 150 may detect this pressure signal and provide an error indication as a result.

In an illustrative embodiment, the base adhesive 152 may be a releasable adhesive allowing removal of the connector 116. If the drape aperture 115 is improperly formed, the connector 116 may be de-coupled from the drape 114 and the drape aperture 115 may be formed to the suitable size and shape, for example, to have a size and shape similar to the size and shape of the cavity aperture 166. The connector 116 may then be re-coupled to the drape 114 so that the distal end 184 may be aligned with a medial portion of the drape aperture 115. Reduced pressure may then be reapplied to the connector 116 through the conduit 110.

Figure 6A:
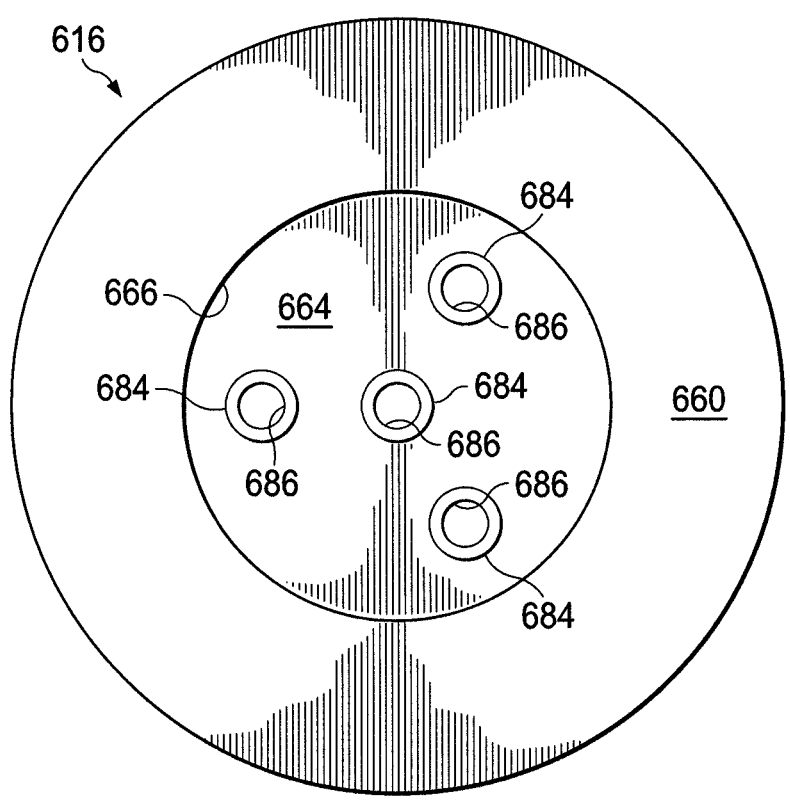
FIG. 6A is a bottom view of another reduced-pressure interface in accordance with an embodiment.
Figure 6B:
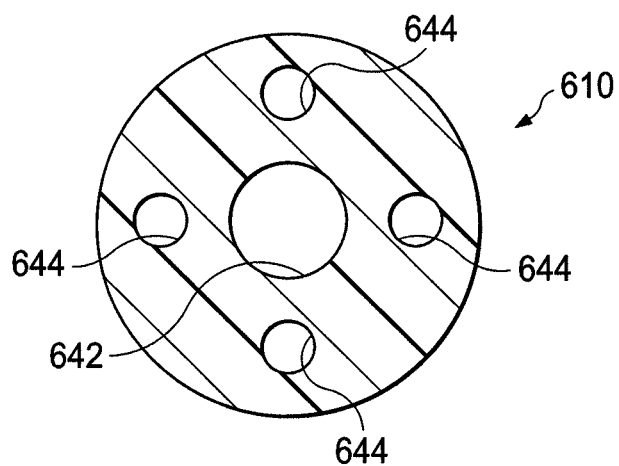
FIG. 6B is a cross-sectional view of another illustrative conduit that may be used with the system of FIG. 1 in accordance with an embodiment.

FIG. 6A is a bottom view of an alternative connector 616, and FIG. 6B is a sectional view through an alternative conduit 610. Connector 616 may be similar to connector 116 described above and modified as described in more detail below. The connector 616 includes a connector body having a cavity 664 including a cavity aperture 666 at one end of the connector body, a conduit port extending from the other end of the connector body and fluidly coupled to the cavity 664, and a base 660 extending from a peripheral portion of the connector body adjacent the cavity aperture 666. The conduit port includes an aperture for receiving the conduit 610. The connector body, the cavity 664, the cavity aperture 666, the conduit port, the aperture, and the base 660 may be structurally and operationally similar to the connector body 162, the cavity 164, the cavity aperture 166, the conduit port 168, the aperture 170, and the base 160 described above with respect to FIGS. 2A-2C.

The connector 616 includes one or more sensing probes having distal ends 684 and probe lumens 686. The sensing probes, the distal ends 684, and the probe lumens 686 may be similar to the sensing probe 180 and the distal end 184 described above with respect to FIGS. 2A-2C. In the illustrated embodiment, the connector 616 includes four sensing probes having distal ends 684 and probe lumens 686. Each sensing probe may be structurally modified so that each distal end 684 may be disposed at separate locations of cavity aperture 666. In the illustrated embodiment, a distal end 684 may be positioned proximate to a medial portion of cavity aperture 666, and each of the other three distal ends 684 may be equidistantly distributed relative to the medial portion of cavity aperture 666. Each sensing probe associated with a respective distal end 684 may be modified so that the distal end 684 may be disposed at the desired location.

As shown in FIG. 6B, the conduit 610 may include a primary lumen 642 and one or more secondary lumens 644. In the illustrated embodiment, four secondary lumens 644 are shown. The primary lumen 642 and the secondary lumens 644 may be structurally and operationally similar to the primary lumen 142 and the secondary lumen 144 of FIG. 2C. When the conduit 610 is coupled to the conduit port of the connector 616, the primary lumen 642 may be fluidly coupled to the cavity 664, and each secondary lumen 644 may be fluidly coupled to a separate probe lumen 686. Inclusion of the additional sensing probes provides additional redundancy for the connector 616. In addition, in the event that the cavity aperture 666 is misaligned with a properly sized drape aperture 115 of the drape 114 of FIG. 2A, the additional sensing probes may allow the pressure sensors 151 of the treatment unit 150 to determine the misalignment by identifying a particular sensing probe where the communicated pressure differs from the expected pressure.

Figure 7:
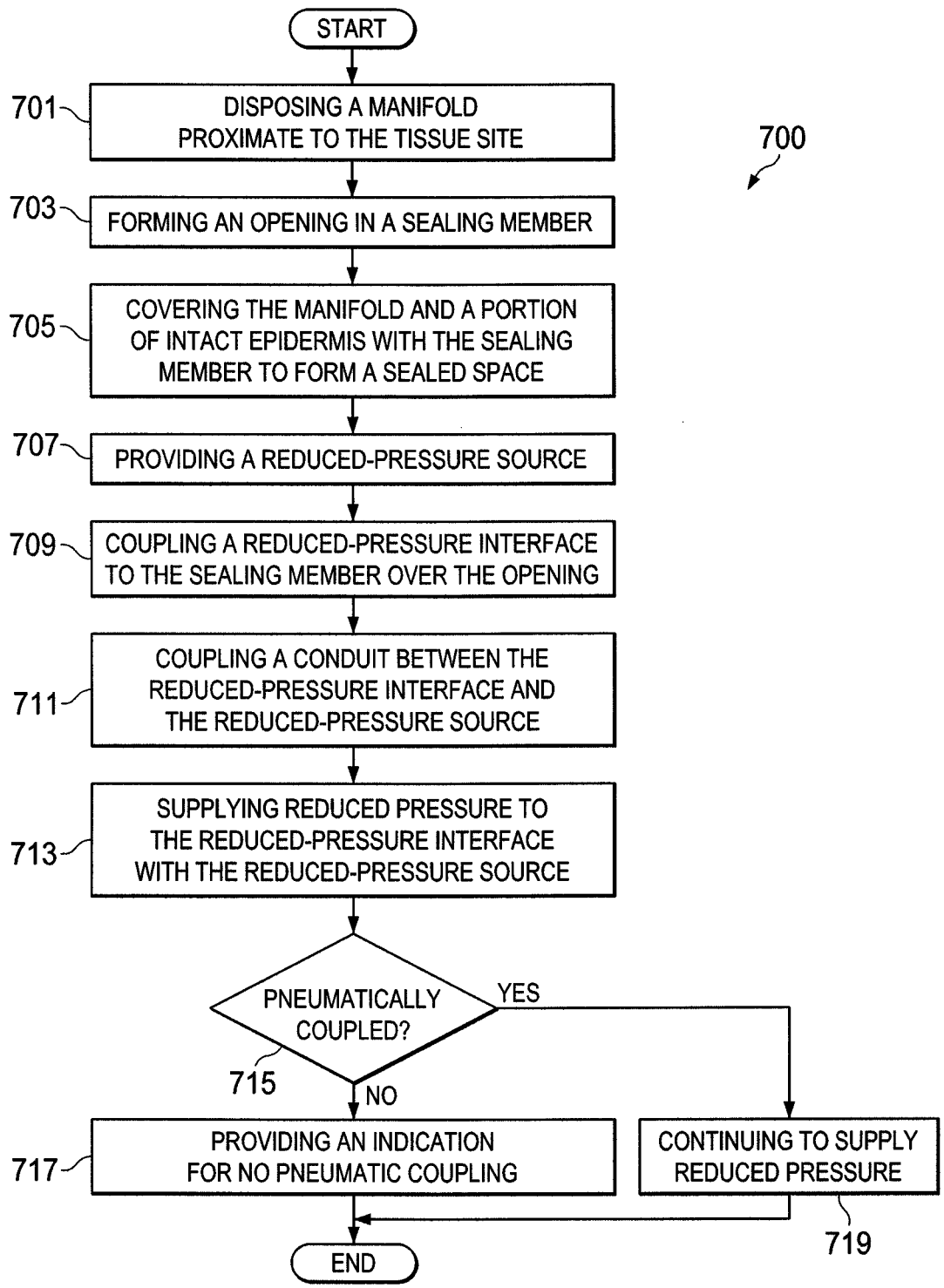
FIG. 7 is a high-level flow chart depicting operational steps of a method for using the system of FIG. 1 in accordance with an embodiment.

FIG. 7 illustrates a high-level flow chart 700 that depicts logical operational steps performed by, for example, the system 100 of FIG. 1, which may be implemented in accordance with an embodiment. As indicated at block 701, the process begins, wherein the system 100 disposes a distribution manifold proximate to the tissue site. For example, the manifold 112 may be disposed proximate to the tissue site 102. Next, at block 703, an aperture may be formed in a sealing member. For example, the drape aperture 115 may be formed in the drape 114, the drape aperture 115 having a size and shape substantially similar to the size and shape of the cavity aperture 166.

The process continues at block 705 where the system 100 covers the manifold and a portion of the epidermis surrounding the tissue site that may be intact with a drape to form a sealed space. For example, the manifold 112 and a portion of the epidermis 124 surrounding the tissue site 102 that may be intact may be covered with the drape 114 to form the sealed space 132. Next, at block 707, the system 100 provides a reduced-pressure source; for example, the system 100 provides the treatment unit 108 having the reduced-pressure source 140. As indicated at block 709, the system then couples a connector proximate to the first side of the sealing member, and at block 711 couples a conduit between the reduced-pressure source and the connector. For example, the connector 116 may be coupled to the drape 114 so that the distal end 184 of the sensing probe 180 may be proximate to a medial portion of the drape aperture 115 of the drape 114 and adjacent to the exposed surface 129 of the manifold 112. The conduit 110 may be coupled between the connector 116 and the treatment unit 108. At block 713, the process continues wherein the system 100 supplies reduced pressure to a cavity of the connector and pneumatically couples the cavity to a sensing probe of the connector. For example, the treatment unit 108 supplies reduced pressure to the connector 116 through the conduit 110 and pneumatically couples the cavity 164 of the connector 116 to the sensing probe 180 of the connector 116.

As indicated at decision block 715, in the event that pneumatic coupling does not occur, the system 100 continues to block 717, where the system 100 provides an indication that the cavity did not pneumatically couple to the sensing probe. For example, the treatment unit 108 may provide an indication that pneumatic coupling did not occur. As indicated at decision block 715, in the event that pneumatic coupling does occur, the system 100 continues to block 719, where the system 100 continues to supply reduced pressure to the reduced pressure interface. For example, the treatment unit 108 may continue to provide reduced pressure to the connector 116.

Figure 8:
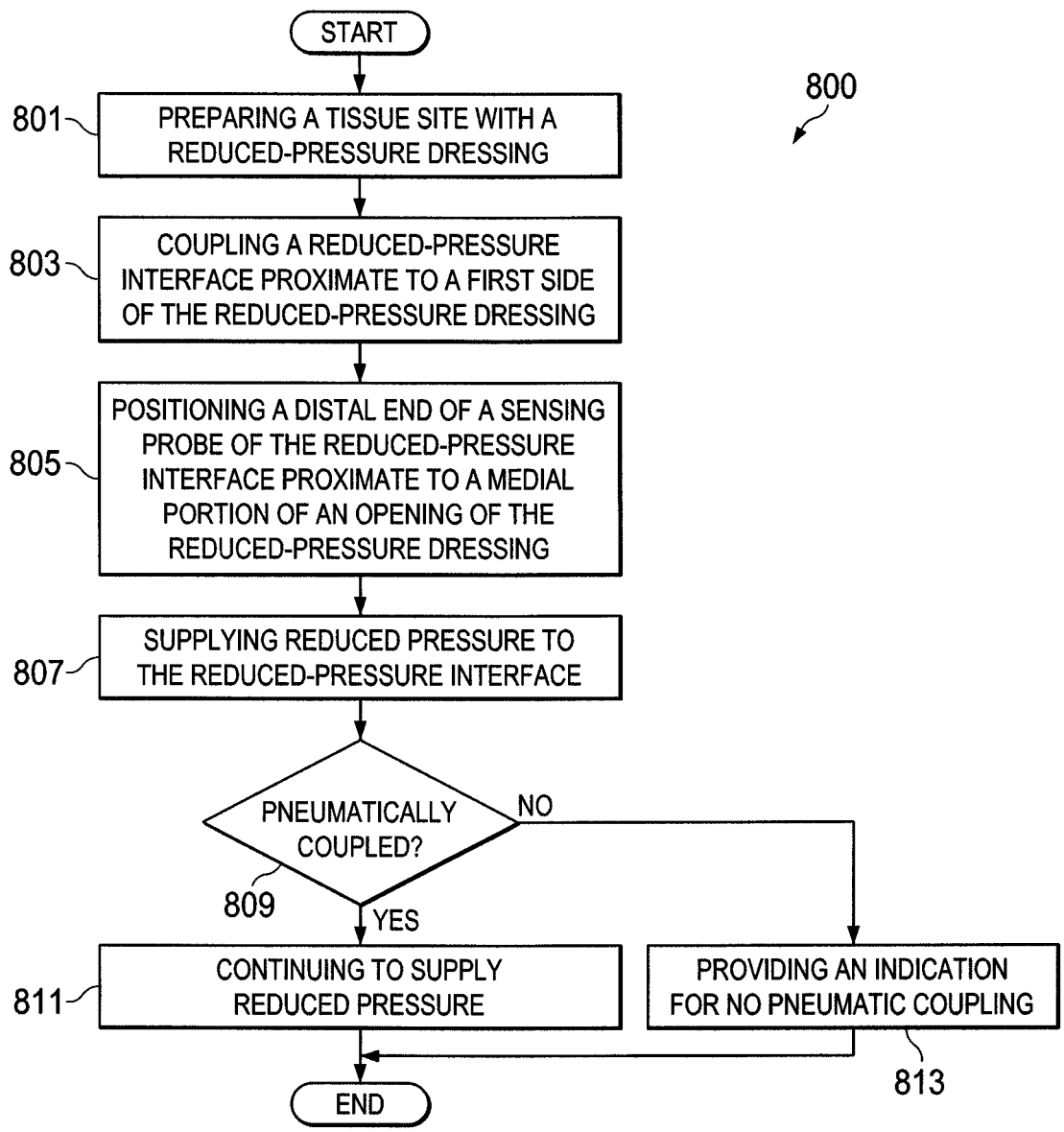
FIG. 8 is a high-level flow chart depicting operational steps of a method for using the system of FIG. 1 in accordance with an embodiment.

FIG. 8 illustrates a high-level flow chart 800 that depicts logical operational steps performed by, for example, the system 100 of FIG. 1, which may be implemented in accordance with an embodiment. As indicated at block 801, the process begins, wherein the system 100 prepares a tissue site with a reduced-pressure dressing. For example, the tissue site 102 may be prepared with the dressing 106. Next, at block 803, the system 100 then couples a connector proximate to the first side of the dressing 106, and at block 805 positions a distal end of a sensing probe of the connector proximate to a medial portion of an aperture of the reduced-pressure dressing. For example, the connector 116 may be coupled to the drape 114 of the dressing 106, and the distal end 184 of the sensing probe 180 may be positioned proximate to a medial portion of the drape aperture 115 of the drape 114 of the dressing 106.

At block 807, the process continues wherein system 100 supplies reduced pressure to the connector to pneumatically couple the supply of reduced pressure to the sensing probe of the connector. For example, the treatment unit 108 supplies reduced pressure to the connector 116 through the conduit 110 to pneumatically couple the cavity 164 of the connector 116 with the sensing probe 180 of the connector 116.

As indicated at decision block 809, the system 100 determines whether pneumatic coupling occurs, and in the event that pneumatic coupling does occur, the system 100 continues to block 811, where the system 100 continues to supply reduced pressure to the reduced pressure interface. For example, the treatment unit 108 may continue to provide reduced pressure to the connector 116 As indicated at decision block 809, in the event that pneumatic coupling does not occur, the system 100 continues to block 813, where the system 100 indicates failure to pneumatically couple. For example, the treatment unit 108 may provide an indication that pneumatic coupling did not occur.

Accordingly, the reduced-pressure treatment apparatus, system, and method may provide notification of improper application of reduced-pressure to a tissue site. In addition, the reduced-pressure treatment system may provide notification of improper formation of an aperture in a dressing that may prevent proper application of reduced pressure. Still further, the reduced-pressure treatment system may provide notification of incorrect placement of a connector relative to the dressing. The reduced-pressure treatment system may also provide notification that an aperture through the dressing may not be of sufficient size.

Although embodiments and their advantages have been described in the context of certain illustrative, non-limiting examples, it should be understood that various changes, substitutions, permutations, and alterations can be made without departing from the scope of the embodiments as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of some illustrative embodiments of the invention. Although various embodiments of the invention have been described above with a certain degree of particularity, or with reference to one or more individual illustrations, those skilled in the art could make numerous alterations to the disclosed embodiments without departing from the scope of the claims.

What is claimed:

1. A connector for fluidly coupling a conduit and a manifold of a reduced-pressure treatment system, the connector comprising:
   a connector body having a cavity including a cavity aperture at a first end of the connector body;
   a conduit port extending from a second end of the connector body and configured to fluidly couple an end of a primary lumen of the conduit to the cavity and to fluidly couple an end of at least one secondary lumen to the connector body;
   a base extending from a peripheral portion of the connector body adjacent to the cavity aperture and configured to be positioned adjacent to a drape covering the manifold, wherein the cavity is configured to be fluidly coupled to the manifold through an aperture formed in the drape; and
   a sensing probe having a probe lumen, a proximal end configured to fluidly couple the at least one secondary lumen to the probe lumen, and a distal end extending to the cavity aperture, wherein the distal end is configured to be positioned adjacent to the manifold, the probe lumen configured to be pneumatically coupled to the manifold and fluidly isolated from direct pneumatic coupling with the cavity.

2. The connector of claim 1, wherein the distal end of the sensing probe extends from the cavity to a plane occupied by the base.

3. The connector of claim 1, wherein the distal end of the sensing probe extends from the cavity past a plane occupied by the base.

4. The connector of claim 1, wherein the sensing probe comprises an elbow.

5. The connector of claim 1, wherein:
   the sensing probe comprises more than one sensing probe, each sensing probe having a distal end spaced-apart from the distal ends of adjacent sensing probes; and
   the at least one secondary lumen comprises more than one secondary lumen, each sensing probe pneumatically coupled to a separate secondary lumen.

6. The connector of claim 5, wherein the more than one sensing probe comprises four sensing probes.

7. The connector of claim 6, wherein:
   one sensing probe of the four sensing probes is positioned so that a distal end of the sensing probe is disposed proximate to a medial portion of the cavity aperture; and
   three of the sensing probes are positioned so that distal ends of each of the sensing probes are spaced-apart from the one sensing probe.

8. The connector of claim 7, wherein the distal end of each sensing probe is equidistantly spaced from the distal ends of adjacent sensing probes.

9. A connector for fluidly coupling a manifold to a reduced-pressure source, the connector comprising:
   a base having an aperture;
   a conduit port configured to receive a primary lumen and a secondary lumen;
   a connector body having a cavity fluidly coupling the aperture to the conduit port; and
   a sensing probe disposed in the cavity, the sensing probe having a probe lumen configured to be pneumatically coupled to the manifold and to the conduit port, the sensing probe fluidly isolated from direct pneumatic coupling with the cavity.

10. The connector of claim 9, wherein the cavity is configured to fluidly couple the aperture to the primary lumen.

11. The connector of claim 9, wherein the sensing probe is configured to pneumatically couple the aperture to the secondary lumen.

12. The connector of claim 9, wherein the sensing probe comprises an elbow disposed between the aperture and the conduit port.

13. The connector of claim 9, wherein the sensing probe comprises a distal end that extends through the aperture past the base.

14. The connector of claim 9, wherein:
the cavity is configured to fluidly couple the manifold to the primary lumen through a drape; and
the sensing probe is configured to pneumatically couple the manifold to the secondary lumen.

15. The connector of claim 9, wherein:
the cavity is configured to fluidly couple the aperture to the primary lumen;
the sensing probe is configured to pneumatically couple the manifold to the secondary lumen through a drape; and
the aperture is configured to couple the cavity to the manifold through the drape.

\* \* \* \* \*